(12) United States Patent
Hengerer et al.

(10) Patent No.: US 10,667,719 B2
(45) Date of Patent: Jun. 2, 2020

(54) MEDICAL IMAGING APPARATUS WITH A POSITIONING UNIT, AND A METHOD FOR DETERMINING A POSITION ON A POSITIONING SURFACE THEREOF

(71) Applicant: Siemens Healthcare GmbH, Erlangen (DE)

(72) Inventors: Arne Hengerer, Moehrendorf (DE); Eva Rothgang, Nuremberg (DE)

(73) Assignee: Siemens Healthcare GmbH, Erlangen (DE)

( * ) Notice: Subject to any disclaimer, the term of this patent is extended or adjusted under 35 U.S.C. 154(b) by 679 days.

(21) Appl. No.: 15/216,737

(22) Filed: Jul. 22, 2016

(65) Prior Publication Data

US 2017/0020409 A1 Jan. 26, 2017

(30) Foreign Application Priority Data

Jul. 23, 2015 (DE) .......................... 10 2015 213 935

(51) Int. Cl.
*A61B 5/055* (2006.01)
*A61B 90/00* (2016.01)
(Continued)

(52) U.S. Cl.
CPC ............ *A61B 5/0555* (2013.01); *A61B 5/684* (2013.01); *A61B 5/704* (2013.01); *A61B 90/39* (2016.02);
(Continued)

(58) Field of Classification Search
CPC ....... A61B 5/0555; A61B 5/684; A61B 90/39; A61B 5/704; A61B 2090/3945;
(Continued)

(56) References Cited

U.S. PATENT DOCUMENTS

| 6,317,619 | B1 * | 11/2001 | Boernert | ............. | G01R 33/341 |
| | | | | | 324/307 |
| 2003/0016015 | A1 * | 1/2003 | Eggers | .................. | G01R 33/28 |
| | | | | | 324/307 |

(Continued)

FOREIGN PATENT DOCUMENTS

| GB | 2443432 A | 5/2008 |
| JP | 2006334096 A | 12/2006 |
| WO | WO-2008142629 A2 | 11/2008 |

OTHER PUBLICATIONS

Lu et al., "Biopsy of Hepatic Dome Lesions: Semi-Real-Time Coronal MR Guidance Technique," American Journal of Roentgentechnology, vol. 168, No. 3, pp. 737-739 (1997).

*Primary Examiner* — Sanjay Cattungal
(74) *Attorney, Agent, or Firm* — Schiff Hardin LLP

(57) ABSTRACT

A medical imaging apparatus is designed to acquire medical imaging data of a patient during a medical imaging examination and has a medical data acquisition scanner, which has a patient reception area at least partially enclosed by the scanner, inside of which a body area of a patient for examination is situated during the medical imaging examination. A positioning unit has a projector and at least one positioning surface situated inside the patient reception area. The projector is designed to project at least one item of anatomical information onto the at least one positioning surface inside the patient reception area.

20 Claims, 2 Drawing Sheets

(51) Int. Cl.
*A61B 5/00* (2006.01)
*G01R 33/28* (2006.01)
*G16H 40/63* (2018.01)
*G01R 33/341* (2006.01)

(52) U.S. Cl.
CPC ........... *G01R 33/283* (2013.01); *G16H 40/63* (2018.01); *A61B 2090/3945* (2016.02); *G01R 33/285* (2013.01); *G01R 33/341* (2013.01)

(58) Field of Classification Search
CPC .... G16H 40/63; G01R 33/283; G01R 33/285; G01R 33/341
USPC .................................................. 600/407–430
See application file for complete search history.

(56) References Cited

U.S. PATENT DOCUMENTS

| | | | |
|---|---|---|---|
| 2004/0242993 A1* | 12/2004 | Tajima | G01R 33/285 600/417 |
| 2009/0024020 A1 | 1/2009 | Swaminathan et al. | |
| 2010/0198112 A1* | 8/2010 | Maad | A61B 6/0457 600/595 |
| 2011/0046481 A1* | 2/2011 | Mate | A61N 5/1049 600/427 |
| 2011/0105895 A1* | 5/2011 | Kornblau | A61B 34/20 600/426 |
| 2011/0122229 A1* | 5/2011 | Cinquin | A61B 1/00193 348/47 |
| 2011/0164728 A1* | 7/2011 | Tsuchiya | A61B 6/037 378/62 |
| 2012/0046521 A1* | 2/2012 | Hunter | A61B 1/2676 600/104 |
| 2013/0060146 A1 | 3/2013 | Yang et al. | |
| 2013/0085377 A1 | 4/2013 | Barbot et al. | |
| 2013/0165767 A1* | 6/2013 | Darrow | G01R 33/543 600/414 |
| 2013/0218024 A1 | 8/2013 | Boctor et al. | |
| 2013/0279779 A1* | 10/2013 | Darrow | G01R 33/543 382/131 |
| 2014/0125337 A1* | 5/2014 | Lee | G01R 33/307 324/309 |
| 2015/0085261 A1* | 3/2015 | Lee | G01R 33/283 353/79 |
| 2015/0148660 A1 | 5/2015 | Weiss et al. | |
| 2015/0366527 A1* | 12/2015 | Yu | A61B 5/055 382/131 |
| 2016/0008620 A1* | 1/2016 | Stubbeman | A61N 2/004 600/14 |
| 2016/0067007 A1* | 3/2016 | Piron | A61B 5/7246 705/3 |
| 2018/0125357 A1* | 5/2018 | Suzuki | A61B 3/113 |
| 2018/0231612 A1* | 8/2018 | Hu | G01R 31/346 |

* cited by examiner

MEDICAL IMAGING APPARATUS WITH A POSITIONING UNIT, AND A METHOD FOR DETERMINING A POSITION ON A POSITIONING SURFACE THEREOF

BACKGROUND OF THE INVENTION

Field of the Invention

The present invention concerns a medical imaging apparatus designed to acquire medical imaging data of a patient during a medical imaging examination. The medical imaging apparatus has a scanner with a patient reception area at least partially enclosed by the scanner, and a positioning unit. The invention also concerns a method for determining a position on a positioning surface which is arranged inside a patient reception area of a medical imaging apparatus during a medical imaging examination.

Description of the Prior Art

In interventional imaging examinations, in particular interventional magnetic resonance examinations such as a magnetic resonance-guided biopsy or a magnetic resonance-guided ablation, etc., it has been customary for the patient to be outside a patient reception area of a medical imaging apparatus for the interventional procedure and to be inside the patient reception area for monitoring the interventional procedure by operation of the imaging apparatus. For this purpose, the patient is typically moved into the patient reception area a number of times and also moved out again. This has been necessary because the confined space inside the patient reception area precludes the precise positioning of an intervention unit, for example a needle, on the patient.

SUMMARY OF THE INVENTION

An object of the present invention is to provide a medical imaging apparatus that facilitates a simple and time-saving interventional imaging examination.

The invention concerns a medical imaging apparatus that is designed to acquire medical imaging data of a patient during a medical imaging examination, that has a scanner, a patient reception area at least partially enclosed by the scanner, inside of which a body area of a patient for examination can be arranged during the medical imaging examination, and a positioning unit having a projector and at least one positioning surface that is arranged inside the patient reception area, wherein the projector is designed to project at least one item of anatomical information onto the at least one positioning surface inside the patient reception area.

As used herein, a scanner is a unit designed to acquire raw data that can be transformed into medical imaging data. In an embodiment of the medical imaging apparatus as a magnetic resonance apparatus, the scanner is a magnet that has a basic field magnet, a gradient coil arrangement and a radio-frequency antenna. A patient reception area means an area inside the scanner designed to receive a body area of the patient for examination during the medical imaging examination. The patient reception area may be cylindrical in design.

A positioning surface means a surface that has at least one positioning element that indicates and/or marks a defined position for a user among the medical personnel. The defined position here may be a position for an interventional procedure, for example, such as a biopsy or an ablation, etc.

The anatomical information may be an image of a relevant body area for the medical imaging examination, such as an image of an organ, etc.

As a result of the invention, during an interventional procedure a position can be displayed for medical personnel, for example a physician supervising and/or performing the interventional imaging examination, by the projection of the at least one item of anatomical information. The at least one item of anatomical information is projected inside the patient reception area such that this area and/or this position is visible from outside to medical personnel for the interventional procedure and is therefore observable unaided by a direct line of sight from outside for the interventional procedure. "Unaided" means that no intervening component such as a mirror or an optical cable or waveguide, is needed in order to view the projected display site from outside of the patient reception area. In addition, advantageous support for medical personnel is provided thereby during an interventional imaging examination, so as to enable a simple and time-saving interventional imaging examination. In addition, repeated retraction and extension of the patient into or out of the patient reception area during the interventional imaging examination may be advantageously avoided as a result of the invention because the interventional procedure inside the patient reception area can also take place, with the patient being located in an examination position in relation to the scanner.

Furthermore, in accordance with the positioning unit has at least one deflection unit that is arranged inside the beam path of the projection radiation of the projector proceeding from the projector to the at least one projection surface. Projection radiation means radiation that includes and/or represents the at least one item of anatomical information during projection onto the positioning surface. Preferably the projection radiation can be radiated onto border areas of the patient reception area by the deflection unit and projected onto the patient, and/or a supplementary unit positioned on the patient, by the deflection unit. The deflection unit preferably is a deflection mirror.

The at least one positioning surface may be a body surface of the patient, enabling the at least one item of anatomical information to always be projected and/or represented on the correct body position of the patient.

Alternatively or in addition, the at least one positioning surface may be a surface of a local radio-frequency antenna unit. This is particularly advantageous when the body area of the patient to be examined, in particular the body area intended for an interventional procedure during the medical imaging examination, such as a magnetic resonance examination, is at least partially covered by the local radio-frequency antenna unit. In addition, it may be advantageous for the at least one positioning surface to be situated inside an aperture of the local radio-frequency antenna unit. Preferably the aperture of the local radio-frequency antenna unit is specially designed to enable the interventional procedure during the medical imaging examination, in particular the magnetic resonance examination, without having to remove the local radio-frequency antenna unit from the patient and then reposition it each time.

In a further embodiment of the invention, the positioning unit has at least one marking element arranged in an area of the positioning surface. This allows a simple and time-saving adjustment and/or focusing of the projection radiation onto the positioning surface. In addition, the marking elements can establish, an intervention area for the interventional procedure on the patient with particular precision inside the patient reception area during the medical imaging examination, in particular the magnetic resonance examination. An area of the positioning surface should be understood to mean an area that is on the positioning surface, and the at least one marking element on the positioning surface can display a projection area for the at least one item of anatomical information.

A particularly cost-effective positioning unit can be provided if the at least one marking element is an infrared reflector element. In addition, by the use of infrared radiation as the marking radiation, an adverse effect and/or impairment of the projection radiation during projection of the at least one item of anatomical information can be prevented. In the embodiment of the at least one marking element as a reflector element and therefore as a passive marking element, furthermore an adverse effect on the medical imaging examination, for example a magnetic resonance examination, can be advantageously avoided. Preferably the infrared reflector element is a surface coating that produces a reflection of infrared radiation.

The positioning unit can have two or more marking elements that are arranged around an area of the projected (at least one) anatomical item of information. This enables the particularly precise determination of the projection area and/or presentation area for the projection of the at least one item of anatomical information. In addition, the position for the interventional procedure can be determined with particular precision. Here, for example, the precise position of the projection surface and/or presentation surface for the at least one item of anatomical information can be determined and/or established from the signals of the two or more marking elements with the use of a triangulation calculation. In addition, the precise position for the interventional procedure can be determined and/or established by the triangulation calculation.

In a further embodiment of the invention the positioning unit has a signal generator. The signal generator preferably is an infrared signal generator, so that an adverse effect and/or impairment of projection radiation during projection of the at least one item of anatomical information can be prevented. In addition, a particularly cost-effective positioning unit can be provided when the signal generator, in particular the infrared signal generator, is an infrared light-emitting diode (infrared LED). In addition, a pulsed positioning signal can be advantageously generated by the infrared LED.

In a further embodiment of the invention, the positioning unit has at least one signal detector. The signal detector preferably is an infrared signal detector. This facilitates simple detection of positioning signals that are preferably emitted and/or reflected by the at least one marking element. The positioning unit can have two or more signal detectors, in particular two or more infrared signal detectors, so that detection from different positions and/or perspectives can be facilitated and consequently particularly precise positioning, for example with the use of triangulation, can be achieved. In addition, systemic errors during positioning can be minimized particularly easily by this embodiment. This can be achieved particularly easily when the at least one signal detector is an infrared camera.

In a further embodiment of the invention, the positioning unit has a position determining processor designed to ascertain the position of an area of the positioning surface with reference to detected position signals. This enables the direct ascertainment and/or determination of the position of the area, in particular of a presentation area and/or a projection area for the projection of the at least one item of anatomical information. In addition, the precise determination of an intervention area for the interventional procedure on the patient inside the patient reception area during the medical imaging examination is facilitated.

The position determining processor has the necessary software and/or computer programs for this purpose. The software and/the computer programs for determining the position can be stored in a memory of a system control computer of the medical imaging apparatus. It is also conceivable for the software and/or computer programs for determining the position to be stored in a separate memory. To ascertain a position, the software and/or computer programs are executed in the processor, which may be formed by the system control computer of the medical imaging apparatus. It is also conceivable for the software and/or computer programs to be executed by a separate processor to determine the position.

The invention also encompasses a method for determining the position of an area of a positioning surface, wherein the positioning surface is situated inside a patient reception area of a medical imaging apparatus during a medical imaging examination that has the following steps.

At least one positioning signal is emitted by at least one signal generator.

At least one reflected positioning signal is detected by at least one signal detector.

The position of the area of the positioning surface is determined with reference to the at least one detected positioning signal, by a position determining processor.

At least one item of position information is projected onto the area by a projector that is in communication with the position determining processor.

The at least one positioning signal is preferably an infrared signal. The signal generator is preferably an infrared signal generator and the signal detector is then an infrared signal detector.

As a result of the invention, during an interventional procedure a position can be displayed particularly advantageously for a member of the medical staff, for example a physician supervising and/or performing the interventional imaging examination, by the projection of the at least one item of anatomical information. The at least one item of anatomical information is projected inside the patient reception area such that this area and/or this position is visible from outside to the medical personnel for the interventional procedure, and is therefore accessible from outside for the interventional procedure. In addition, advantageous support for medical personnel is provided by this means during an interventional imaging examination, in particular thus enabling a simple and time-saving interventional imaging examination. In addition, repeated retraction and extension of the patient into or out of the patient reception area during the interventional imaging examination can be advantageously avoided as a result of this invention, as the interventional procedure inside the patient reception area can also take place hereby, wherein the patient can be located in an examination position in relation to the scanner.

The advantages of the method according to the invention for determining a position of an area of a positioning surface essentially correspond to the advantages of the medical imaging apparatus according to the invention, which are explained in detail above. Features, advantages or alternative embodiments of the apparatus are also applicable to the method.

DESCRIPTION OF THE PREFERRED EMBODIMENTS

Figure 1:
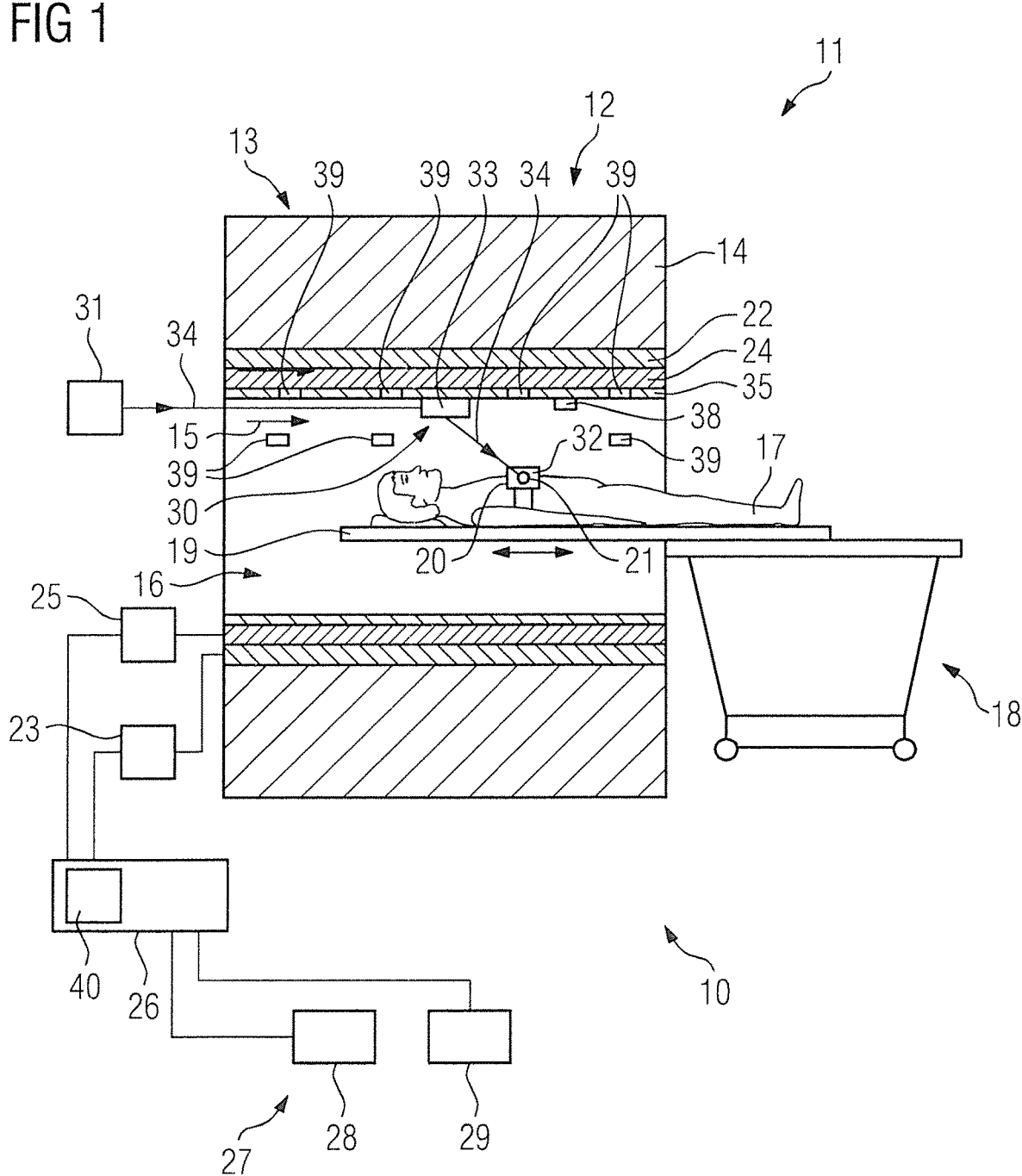
FIG. 1 schematically illustrates a medical imaging apparatus according to the invention.

FIG. 1 is a schematic illustration of a medical imaging apparatus. The medical imaging apparatus 10 is formed in the present exemplary embodiment as a magnetic resonance apparatus 11, so the present invention is explained in exemplary manner with reference to the magnetic resonance apparatus 11. The present invention is not restricted to the embodiment of the medical imaging apparatus as a magnetic resonance apparatus 11 and further modalities of the medical imaging apparatus are conceivable.

The magnetic resonance apparatus 11 has a scanner 13 formed by a magnet unit that has a superconducting basic field magnet 14 for the generation of a strong and constant basic magnetic field 15. The magnetic resonance scanner 13 has a patient reception area 16 for the reception of a patient 17. The patient reception area 16 in the present exemplary embodiment is cylindrical in design and cylindrically enclosed by the scanner 13 in a circumferential direction. Embodiments of the patient reception area 16 deviating from this are also possible.

The patient 17 can be moved into the patient reception area 16 by a patient positioning device 18 of the magnetic resonance apparatus 11. A body area of the patient for examination 17 is moved inside the patient reception area 16. The patient positioning device 18 has a movable patient table 19 inside the patient reception area 16 for this purpose.

Figure 2:
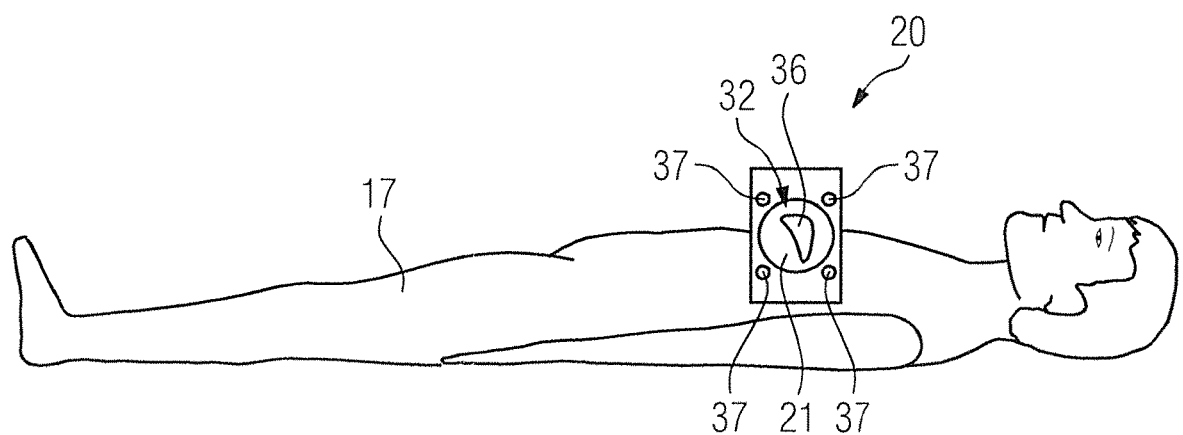
FIG. 2 schematically illustrates an embodiment of a positioning surface of a positioning unit.

In the exemplary embodiment, a local radio-frequency antenna 20 of the magnetic resonance scanner 13 is arranged on the body area of the patient 17 for examination. In the exemplary embodiment the local radio-frequency antenna 20 is designed for an interventional procedure on the patient 17, and thus has an aperture 21 therein for the interventional procedure (FIGS. 1 and 2).

The scanner 13 also a radio-frequency antenna 24, in the form of a body coil that is built into the scanner 13. Typically, the radio-frequency antenna 24 is used to radiate radio-frequency energy into a designated region of the patient 17, in order to cause nuclear spins in the patient 17 to deviate from the polarization of the nuclear spins produced by the basic magnetic field 15, thereby causing the nuclear spins to emit magnetic resonance signals. Typically, those magnetic resonance signals are detected by the local radio-frequency antenna 20. It is also possible, however, for either of the radio-frequency antenna 24 or the local radio-frequency antenna 20 to be used both for transmission and reception of radio-frequency signals.

The scanner 13 has a gradient coil arrangement 22 for the generation of magnetic field gradients that are used for spatial coding during imaging. The gradient coil arrangement 22 is controlled by a gradient control processor 23 of the magnetic resonance apparatus 11. The radio-frequency antenna 24 is controlled by a radio-frequency antenna controller 25 to emit radio-frequency magnetic resonance sequences into an examination volume that is essentially formed by the patient reception area 16 of the magnetic resonance scanner 13.

The magnetic resonance apparatus 11 has a system control computer 26 to control the basic field magnet 14, the gradient control processor 22 and the radio-frequency antenna controller 23. The system control computer 26 controls the magnetic resonance apparatus 11 centrally, for example for the performance of a predetermined imaging gradient echo sequence. In addition, the system control computer 26 can be configured to evaluate medical imaging data acquired during the magnetic resonance examination.

The magnetic resonance apparatus 11 has a user interface 27 connected to the system control computer 26. Control information such as imaging parameters and reconstructed magnetic resonance images can be displayed on a display monitor 28, for example on at least one monitor, of the user interface 27 for the medical personnel. Furthermore, the user interface 27 has an input unit 29 via which information and/or parameters can be entered by the medical personnel during a measurement procedure.

The magnetic resonance apparatus 11 has a positioning unit 30 that has a projector 31, a positioning surface 32 and a deflection unit 33. The projector 31 is arranged outside the patient reception area 16 and is designed to project projection radiation 34 into the patient reception area 16, in particular onto the positioning surface 32.

The positioning surface 32 is arranged inside the patient reception area 16. During a magnetic resonance-guided intervention on the patient 17 a position for an interventional procedure is marked, or established by the positioning surface 32 inside the patient reception area 16. The positioning surface 32 in the present exemplary embodiment is a surface of the local radio-frequency antenna unit 20, and the positioning surface 32 is here situated inside the aperture 21 of the local radio-frequency antenna unit 20. Alternatively or in addition, the positioning surface 32 may include a body surface of the patient 17.

In the exemplary embodiment, the positioning unit 30 has a single positioning surface 32. In an alternative embodiment of the invention, the positioning unit 30 may have two or more positioning surfaces 32.

The deflection unit 33 is situated within the beam path of the projection radiation 34 of the projector 31 from the projector 31 to the projection surface 32. For simple and space-saving beam guidance, the deflection unit 33 is arranged inside the patient reception area 16. The deflection unit 33 is preferably arranged on a housing wall 35 of the patient reception area 16, which is opposite a reclining area of the patient table 19 inside the patient reception area 16 for positioning of the patient 17. The projection radiation 34 radiated from the deflection unit 33 onto the positioning surface 32 has a non-zero beam deflection angle with regard to the projection radiation 34, from the projector 21 onto the deflection unit 33, of at least 75° to 150° maximum, preferably of at least 80° to 130° maximum and particularly advantageously of at least 85° to 120° maximum. In the exemplary embodiment the deflection unit 33 has a deflection mirror, which is not shown in more detail. In an alternative embodiment of the invention the deflection unit 33 may have more than one deflection mirror.

During the magnetic resonance examination, in particular an interventional magnetic resonance examination, one or more items of anatomical information 36 are projected into the patient reception area 16 and onto the positioning surface 32 by the projector 31. The anatomical information 36, for example a visible image or outline of an organ, on which the interventional procedure is to take place, is displayed for medical personnel, for example a physician performing the interventional magnetic resonance examination. In addition, the position for the interventional procedure is displayed to the medical personnel so that the interventional procedure on the patient 17 can take place inside the patient reception area during the medical imaging examination.

For simple and precise positioning of the anatomical information 36 on the positioning surface 32 and/or for precise position specification for the interventional procedure, in addition the positioning unit 30 has at least one marking element 37, one signal generator 38, one signal detector 39 and one position determining unit 40. In the present exemplary embodiment the positioning unit 30 has a number of marking elements 37 that are arranged in one area of the positioning surface 32. The area with the individual marking elements 37 extends around a display area and/or projection area for the display of the anatomical information 36. For the sake of clarity, the marking elements 37 and their arrangement on the local radio-frequency antenna unit 20 are shown in more detail in FIG. 2.

The individual marking elements 37 each include an infrared reflector element for the reflection of infrared radiation. The individual infrared reflector elements have a surface coating that causes the reflection of infrared radiation. In the exemplary embodiment the individual infrared reflector elements are circular in design. In an alternative embodiment a different embodiment of the infrared reflector elements is also conceivable at any time.

The signal generator 38 in the exemplary embodiment is an infrared signal generator that has at least one infrared light-emitting diode (infrared LED). A pulsed positioning signal can be generated by the infrared LED. The infrared signal generator is arranged on the housing wall 35 of the patient reception area 16, but a different placement of the infrared signal generator is also conceivable.

The signal detector 39 in the exemplary embodiment is an infrared signal detector. The infrared signal detector has a number of infrared cameras that are arranged at different positions within the patient reception area 16. The individual infrared cameras can be incorporated inside the housing wall 35 of the patient reception areas 16, but a different placement of the number of infrared cameras is also conceivable.

The position determining unit 40 is designed to determine and/or ascertain a position of the display area and/or an intervention area. To this end, the position determining unit 40 is integrated inside the system control computer 26 and has software and/or computer programs designed for this purpose. The software and/or computer programs for ascertainment of a position are stored in a memory of the system control computer 26 and are executed by a processor of the system control computer 26.

The position determining unit 40 ascertains and/or determines a position of the display area and/or the projection area of the positioning surface 32 with reference to the position signals, in particular the infrared signals, detected by a number of infrared signal detectors. In addition, a position of the intervention area for the interventional procedure on the patient inside the patient reception area of the position determining unit 40 is ascertained and/or determined with reference to the position signals detected by a number of infrared signal detectors, in particular the infrared signals. The position can be determined with the use of triangulation.

Figure 3:
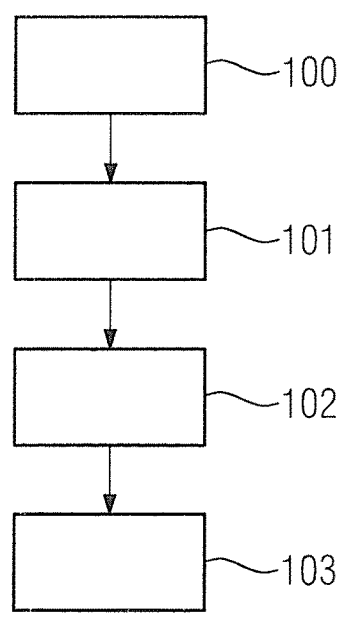
FIG. 3 is a flowchart of a method according to the invention for determining the position of an area of a positioning surface.

FIG. 3 shows a method for determining a position of an area of the positioning surface 32. In a first method step 100, a positioning signal comprising the infrared signal is emitted by means of the infrared signal generator. The infrared signal is reflected by the marking elements 37 and in a further method step 101 the infrared signal reflected by the marking elements 37 is detected by the infrared signal detector.

Afterwards, in a further method step 102 a position of the intervention area is determined and/or ascertained by means of the position determining unit 40. In addition, in the further method step 102 a position of an area of the positioning surface 32 is also determined and/or ascertained by means of the position determining unit 40 with reference to the detected infrared signals. The area of the positioning surface 32 comprises the display area and/or the projection area for the display of the at least one item of anatomical information 36.

On the basis of the determined position of the intervention area, in a further method step 103 a projection of an item of position information of the intervention area for the interventional procedure on the patient 17 is projected by the projector 31. In addition, in the further method step 103 the anatomical information 36 can also be projected onto the presentation surface by the projector 31.

Although modifications and changes may be suggested by those skilled in the art, it is the intention of the inventors to embody within the patent warranted hereon all changes and modifications as reasonably and properly come within the scope of their contribution to the art.

We claim as our invention:

1. A medical imaging apparatus comprising:
   a medical image data acquisition scanner configured to acquire medical imaging data from a patient;
   said medical imaging data acquisition scanner having a reception area at least partially enclosed by said scanner and configured to house the patient to facilitate an acquisition of said medical imaging data of a body area of the patient housable therein; and
   a positioner comprising a projector situated outside the reception area, said projector being configured to project at least one item of anatomical information into the reception area and onto a surface configured to be removably situated on said body area of said patient housable inside said reception area at a projection location inside said reception area that is observable, via a direct, unaided line of sight, to a person outside of said reception area.

2. A medical imaging apparatus as claimed in claim 1 wherein said projector is configured to project a projection beam proceeding along a beam path into the reception area, wherein the positioner further includes a deflector situated inside the reception area and in the beam path, the deflector being configured to deflect said beam from said projector onto said surface configured to be situated on said body area.

3. A medical imaging apparatus as claimed in claim 1 wherein said positioner is further configured to project said at least one item of anatomical information onto a body surface of said body area of the patient housable in the reception area.

4. A medical imaging apparatus as claimed in claim 1 wherein said medical imaging data acquisition scanner is a magnetic resonance imaging data acquisition scanner and comprises a local radio-frequency antenna adapted for placement at a position on the patient, and wherein said positioner is configured to project said at least one item of anatomical information onto a surface of said local radio-frequency antenna, as said surface configured to be situated on said body area.

5. A medical imaging apparatus as claimed in claim 4 wherein said local radio-frequency antenna has an aperture therein, and wherein said positioner is configured to project said at least one item of anatomical information inside of said aperture of said local radio-frequency antenna.

6. A medical imaging apparatus as claimed in claim 1 wherein said positioner comprises at least one marker element situated within said surface configured to be situated on said body area.

7. A medical imaging apparatus as claimed in claim 6 wherein said at least one marking element is an infrared reflector.

8. A medical imaging apparatus as claimed in claim 6 wherein said positioner comprises two or more marking elements configured to be situated around an area of said surface configured to be situated on said body area at which said at least one item of anatomical information is projected.

9. A medical imaging apparatus as claimed in claim 1 wherein said positioner comprises a signal generator that generates and emits radiation.

10. A medical imaging apparatus as claimed in claim 9 wherein said signal generator comprises at least one infrared light-emitting diode.

11. A medical imaging apparatus as claimed in claim 1 wherein said positioner comprises at least one signal detector that detects infrared radiation emitted by said infrared light-emitting diode.

12. A medical imaging apparatus as claimed in claim 1 wherein said at least one signal detector is an infrared camera.

13. A medical imaging apparatus as claimed in claim 11 wherein said positioner comprises a position determining processor configured to ascertain a position of an area of said positioning surface with respect to position signals detected by said at least one signal detector.

14. A medical imaging apparatus as claimed in claim 1, wherein said at least one item of anatomical information includes a representation of anatomy associated with the body area of the patient housable in the reception area.

15. A medical imaging apparatus as claimed in claim 14, wherein the representation of the anatomy includes an outline representation of an organ.

16. A medical imaging apparatus as claimed in claim 14, wherein the representation of an anatomy includes an image of an organ.

17. A medical imaging apparatus as claimed in claim 1, further comprising a local radio-frequency antenna configured to be situated on said body area of the patient housable in the reception area, wherein said local radio-frequency antenna includes said surface in which said at least one item of anatomical information is projected thereon.

18. A method for identifying a position of an area of a patient situated inside a patient reception area of a medical image data acquisition scanner during a medical imaging examination, said method comprising:
 placing a patient on a patient table in a patient reception area of a medical imaging data acquisition scanner, said patient reception area being at least partially enclosed by said scanner, and a body area of the patient being situated in the patient reception area in order to acquire medical imaging data therefrom;
 placing a positioning surface on said body area of the patient; and
 from a projector situated outside the patient reception area, projecting at least one item of anatomical information into the patient reception area and onto said positioning surface placed on said body area of said patient inside the patient reception area at a projection location inside said patient reception area that is observable, via a direct, unaided line of sight, to a person outside of said patient reception area.

19. A method as claimed in claim 18 comprising, from said projector, further projecting said at least one item of anatomical information onto a body surface of the patient within said body area of said patient.

20. A method as claimed in claim 18 comprising placing a local radio-frequency antenna on said body area of the patient in order to participate in acquiring said medical imaging data from said body area, wherein said local radio-frequency antenna includes said positioning surface, and, from said projector, further projecting said at least one item of anatomical information onto said positioning surface of said local radio-frequency antenna.

* * * * *